US008268853B2

(12) United States Patent
Schrimpf et al.

(10) Patent No.: US 8,268,853 B2
(45) Date of Patent: Sep. 18, 2012

(54) 3,9-DIAZASPIRO[5,5]UNDECANE AMIDES AND UREAS AND METHODS OF USE THEREOF

(75) Inventors: Michael R. Schrimpf, Grayslake, IL (US); Diana L. Nersesian, Gurnee, IL (US); Chih-Hung Lee, Vernon Hills, IL (US); Ramin Faghih, Lake Forest, IL (US); Gregory A. Gfesser, Lindenhurst, IL (US)

(73) Assignee: Abbott Laboratories, Abbott Park, IL (US)

( * ) Notice: Subject to any disclaimer, the term of this patent is extended or adjusted under 35 U.S.C. 154(b) by 266 days.

(21) Appl. No.: 12/823,969

(22) Filed: Jun. 25, 2010

(65) Prior Publication Data

US 2010/0331353 A1    Dec. 30, 2010

Related U.S. Application Data

(60) Provisional application No. 61/220,520, filed on Jun. 25, 2009.

(51) Int. Cl.
*A61K 31/438* (2006.01)
*C07D 221/20* (2006.01)

(52) U.S. Cl. ......................... 514/278; 546/16
(58) Field of Classification Search .................... 546/16; 514/278
See application file for complete search history.

(56) References Cited

U.S. PATENT DOCUMENTS

| 5,451,578 | A | 9/1995 | Claremon et al. |
| 5,914,328 | A | 6/1999 | Lin et al. |
| 5,948,793 | A | 9/1999 | Abreo et al. |
| 6,809,105 | B2 | 10/2004 | Schrimpf et al. |
| 6,833,370 | B1 | 12/2004 | Schrimpf et al. |

FOREIGN PATENT DOCUMENTS

| WO | WO9932480 A1 | 7/1999 |
| WO | WO0071534 A1 | 11/2000 |
| WO | WO0181347 A2 | 11/2001 |
| WO | 2005/040167 A1 * | 5/2005 |
| WO | WO2005040167 A1 | 5/2005 |
| WO | WO2005097795 A1 | 10/2005 |
| WO | WO2006006490 A1 | 1/2006 |
| WO | WO2006114400 A1 | 11/2006 |

OTHER PUBLICATIONS

Cheng, Y., et al., "Relationship Between the Inhibition Constant ($K_I$) and the Concentration of Inhibitor Which Causes 50 Per Cent Inhibition ($I_{50}$) of an Enzymatic Reaction," Biochemical Pharmacology, 1973, vol. 22, pp. 3099-3108.

Curtis, L., et al., "Potentiation of Human α4β2 Neuronal Nicotinic Acetylcholine Receptor by Estradiol," Molecular Pharmacology, 2002, vol. 61 (1), pp. 127-135.

Decker, M., et al., "Nicotinic Acetylcholine Receptor Agonists: a Potential New Class of Analgesics," Current Topics in Medicinal Chemistry, 2004, vol. 4 (3), pp. 369-384.

Diaz, G., et al., "The [$^3$H]dofetilide binding assay is a predictive screening tool for hERG blockade and proarrhythmia: Comparison of intact cell and membrane preparations and effects of altering $[K^+]_O$," J. Pharm. and Toxicological Methods, 2004, vol. 50, pp. 187-199.

Dunbar, G., et al., "Effect of Ispronicline, a Neuronal Nicotinic Acetylcholine Receptor Partial Agonist, in Subjects with Age Associated Memory Impairment (AAMI)," Journal of Psychopharmacology, 2007, vol. 21 (2), pp. 171-178.

Ferreira, M., et al., "Brainstem Nicotinic Receptor Subtypes That Influence Intragastric and Arterial Blood Pressures," Journal of Pharmacology and Experimental Therapeutics, 2000, vol. 294 (1), pp. 230-238.

Gopalakrishnan, M., et al., "Ion channels Ligand gated. Comprehensive Medicinal Chemistry II, Edited by Triggle D.J. et al.," Major Reference Works, 2006, Unit 2.22, pp. 877-918, Elsevier.

Higuchi, T., et al., eds., Pro-drugs as Novels Delivery Systems, vol. 14, ACS Symposium Series, 1975, Table of Contents.

Korolkovas, A., "Development of Drugs" in: Essentials of Medicinal Chemistry, Second Edition, John Wiley and Sons, 1988, pp. 97-118.

Lauretti, G., "Highlights in Opioid Agonists and Antagonists," Neurotherapeutics, 2006, vol. 6 (4), pp. 613-622.

Pasternak, G., "Pharmacological Mechanisms of Opioid Analgesics," Clinical Neuropharmacology, 1993, vol. 16 (1), pp. 1-18.

(Continued)

*Primary Examiner* — Rita Desai
(74) *Attorney, Agent, or Firm* — Nancy J. Gettel; Portia Chen

(57) ABSTRACT

Compounds of formula (I)

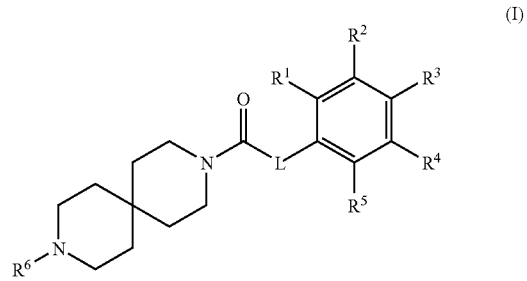

are useful in treating conditions or disorders ameliorated by α4β2 positive allosteric modulators. Also disclosed are pharmaceutical compositions of compounds of formula (I), methods for using such compounds and compositions, and a process for preparing the compounds.

12 Claims, No Drawings

OTHER PUBLICATIONS

Poste, G., et al., "Lipid Vesicles as Carriers for Introducing Biologically Active Materials into Cells," Methods in Cell Biology, 1976, vol. 14, pp. 33-71.

Rice, L., et al., "Spiranes. V (1). A synthetic route to symmetrical and unsymmetrical 3,9-diazaspiro [5.5]undecanes," Journal of Heterocyclic Chemistry, 1964, vol. 1 (3), pp. 125-127.

Roche, E., ed., Bioreversible Carries in Drug Design Theory and Application, Pergamon Press, 1987, Table of Contents.

Wilens, T., et al., "ABT-089, A Neuronal Nicotinic Receptor Partial Agonist, for the Treatment of Attention-Deficit/Hyperactivity Disorder in Adults: Results of a Pilot Study," Biological Psychiatry, 2006, vol. 59 (11), pp. 1065-1070.

Coe, et al., "In pursuit of [alpha] 4 [beta] 2 nicotinic receptor partial agonists for smoking cessation: Carbon analogs of (−)-cytisine", 2005, vol. 15, pp. 2974-2979.

International Search Report for Application No. PCT/US2010/040064, mailed on Mar. 22, 2011, 11 pages.

Roger, et al., "Synthesis of a [2-Pyridinyl-18F]-labelled fluoro derivative of (−)-Cytisine as a candidate radioligand for brain nicotinic [alpha] 4 [beta] 2 receptor imaging with PET", 2003, vol. 11, pp. 5333-5343.

\* cited by examiner

3,9-DIAZASPIRO[5,5]UNDECANE AMIDES AND UREAS AND METHODS OF USE THEREOF

CROSS-REFERENCE TO RELATED APPLICATION

This application claims the benefit of U.S. Provisional Patent Application No. 61/220,520, filed on Jun. 25, 2009, which is herein incorporated by reference in its entirety.

STATEMENT REGARDING FEDERALLY SPONSORED RESEARCH OR DEVELOPMENT

Not applicable.

TECHNICAL FIELD

The invention relates to novel 3,9-diazaspiro[5,5]undecane amide and urea derivatives, compositions comprising such compounds, and methods of preventing or treating conditions and disorders using such compounds and compositions.

DESCRIPTION OF RELATED TECHNOLOGY

The endogenous cholinergic neurotransmitter, acetylcholine (ACh), exerts its biological effect via two types of cholinergic receptors, the muscarinic acetylcholine receptors (mAChR) and the nicotinic acetylcholine receptors (nAChR). nAChRs are pentameric assemblies of subunits surrounding a central pore that gates the flux of $Na^+$, $K^+$ and $Ca^{2+}$ ions. At least 16 subunit proteins, i.e. $\alpha 2$-$\alpha 10$, $\beta 1$-$\beta 10$, $\gamma$, $\delta$ and $\epsilon$, have been identified in neuronal tissues. These subunits provide for a great variety of homomeric and heteromeric combinations that account for the diverse receptor subtypes. For example, functional neuronal nAChR or neuronal nicotinic receptor (NNR) assemblies can be homomeric, comprising $\alpha 7$, $\alpha 8$ or $\alpha 9$ subunits, or heteromeric, usually with at least one subunit from the a group ($\alpha 2$, $\alpha 3$, $\alpha 4$ and $\alpha 6$) and the remainder from the $\beta$ group ($\beta 2$ and ($\beta 4$). In the central nervous system, $\beta 4\beta 2$-containing NNR and $\alpha 7$-containing NNR subtypes are the most widespread and mediate synaptic and, possibly, paracrine functions. These NNRs are expressed at high levels in areas involved with learning and memory, and play key roles in modulating neurotransmission in these regions. Reduced cholinergic activity and dysregulation of NNRs have been correlated with disease states involving cognitive deficits, progressive dementia, and epilepsy. Accordingly, these NNRs are implicated in a range of physiological and patho-physiological functions related to cognitive function, learning and memory, reward, motor control, arousal and analgesia (reviewed in Gopalakrishnan, M. et al., Ion channels-Ligand-gated. Comprehensive Medicinal Chemistry II, Edited by Triggle D. J., et al., Major Reference Works, Elsevier. Unit 2.22, pp 877-918, 2006).

Discovery of the important roles played by NNRs in several CNS disorders has called attention to these membrane proteins and to ligands, or compounds, that are able to modulate, i.e. modify, the function of such membrane proteins. The prototypical NNR agonist, nicotine, has itself been shown to improve attention and cognitive performance, reduce anxiety, normalize sensory gating, and effect neuroprotection. However, nicotine is not sufficiently selective among NNRs and its utility is limited by side effects including seizures, irregular heartbeat, hypertension, and gastrointestinal effects. Accordingly, identification of compounds, agonists or allosteric modulators, that target distinct subtypes to retain the beneficial effects, while eliminating or decreasing adverse effects, continues to be an active area of research.

NNRs, especially $\alpha 4\beta 2$ NNRs, have been targeted for pain, cognitive disorders and various central nervous system diseases. Gene knockout, antisense and pharmacological studies have shown that $\alpha 4$ and $\beta 2$ NNRs are responsible for mediating nicotinic analgesia at supraspinal responses and spinal sites (Decker, M. W., et al., Curr. Top. Med. Chem., 4: 369-384, 2004). Ligands targeting $\alpha 4\beta 2$ NNRs have shown improvement in cognitive and attentive function in preclinical models and, more recently, in human disease states such as attention deficit hyperactivity disorder (ADHD) (Wilens, T. E., et al., Biol. Psychiatry, 59: 1065, 2006) and age-associated memory impairment (Dunbar, G. C., et al., Psychopharmacol., 21: 171, 2007). One aspect of the discovery of novel NNR compounds is to avoid ganglioinic $\alpha 3^*$ NNRs, as the dose-limiting emetic liability of nonselective compounds may be attributed to activation of $\alpha 3$ containing NNRs. $\alpha 3^*$ NNRs in the dorsal motor nucleus of the vagus and in nucleus tractus solitarius have been implicated in gastric and blood pressure responses to nicotine injected locally (Ferreira, M., et al., J. Pharmacol. Exp. Ther. 294:230-238, 2000).

Compounds with varying degrees of selectivity for $\alpha 4\beta 2$ NNRs over other nicotinic subtypes ($\alpha 3$, $\alpha 7$, $\alpha 1$-containing) have been discovered over the years for the treatment of pain and a range of psychiatric and neurological disorders especially involving cognitive deficits in attention, alertness and memory. These may include those conditions that may benefit from selective enhancement of cholinergic transmission such as attention deficit, psychotic disorders, selected pain syndromes, smoking cessation and those thought to involve reduced cholinergic function such as neurodegenerative disorders, central inflammatory or autoimmune disorders, brain trauma and cerebrovascular disease. Modulation of $\alpha 4\beta 2$ NNRs is expected to be beneficial in a number of diseases including Alzheimer's disease, mild cognitive impairment and related syndromes, Lewy body dementia, vascular dementia, attention deficit/attention deficit-hyperactivity disorder, schizophrenia, bipolar and mood disorders, schizoaffective disorders, Tourette's syndrome, brain trauma, Parkinson's disease, Huntington's disease and conditions of substance abuse including alcohol abuse and smoking cessation. Selected pain syndromes includes chronic pain that can be nociceptive, neuropathic, or both and originating from cancer, injury, surgery, or chronic conditions such as arthritis or nerve injury/disease. Neuropathic pain can be peripheral (painful peripheral mononeuropathy and polyneuropathy) or central (post stroke, following spinal cord injury) and can originate from nerve injury following a wide array of conditions/events such as direct trauma to nerves, inflammation/neuritis/nerve compression, metabolic diseases (diabetes), infections (herpes zoster, HIV), tumors, toxins (chemotherapy), and primary neurological diseases.

Treatment with NNR agonists, which act at the same site, as the endogenous transmitter ACh, may be problematic because ACh not only activates, but also inhibits receptor activity through processes that include desensitization. Further, prolonged receptor activation may cause long-lasting inactivation. Thus, uncertainty exists whether chronic treatment with agonists in humans might provide suboptimal benefit due to sustained receptor activation and desensitization of the NNRs. An alternate approach to target $\alpha 4\beta 2$ NNR function is by enhancing effects of the endogenous neurotransmitter acetylcholine via positive allosteric modulation. This approach provides an opportunity to (i) reinforce the endogenous cholinergic neurotransmission without directly activating the receptor like classical agonists, (ii) prevent receptor desensitization (iii) possibly resensitize inactivated receptors. Thus, the spatial and temporal characteristics of endogenous α4β2 receptor activation are preserved unlike agonists that will tonically activate all receptors, leading to a non-physiological pattern of receptor activation.

In light of the evidence supporting the various therapeutic uses of NNRs, it would be beneficial to discover novel allosteric modulators that could provide therapeutic benefits.

SUMMARY OF THE INVENTION

The invention relates to 3,9-diazaspiro[5,5]undecane amide and urea compounds, compositions comprising such compounds, and method of using such compounds and compositions.

In one aspect, the invention is compounds having the formula (I)

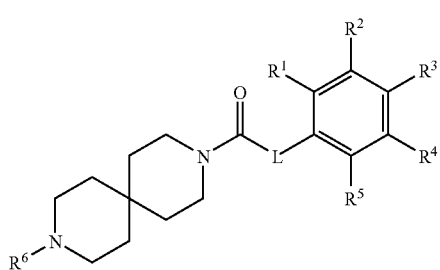

(I)

or a pharmaceutically acceptable salt thereof, wherein L is a bond, $CH_2$, or $NR^7$; $R^1$, $R^2$, $R^3$, $R^4$ and $R^5$ are each independently selected from hydrogen, halogen, and methoxy, wherein at least one of $R^1$, $R^2$, $R^3$, $R^4$ and $R^5$ is halogen and at least one of $R^1$, $R^2$, $R^3$, $R^4$ and $R^5$ is methoxy; $R^6$ is hydrogen or methyl; and $R^7$ is hydrogen or alkyl.

Another aspect of the invention relates to pharmaceutical compositions comprising compounds of formula (I). Such compositions can be administered typically as part of a therapeutic regimen for treatment or prevention of conditions and disorders related to NNR activity.

Yet another aspect of the invention relates to a method of modulating α4β2 NNR activity. The method is useful for treating, preventing or both treating and preventing conditions and disorders related to α4β2 NNR activity, particularly in mammals. Such method is useful for treating, preventing or both treating and preventing conditions and disorders related to α4β2 NNR activity in mammals.

A further aspect of the invention relates to a method of selectively modulating NNR activity, for example α4β2 NNR positive allosteric modulator (PAM) activity, in combination with a nicotinic agonist or partial agonist to improve the tolerability of therapy using such nicotinic agonist or partial agonist.

Yet another aspect of the invention relates to a method for treating, preventing or both treating and preventing pain.

DETAILED DESCRIPTION OF THE INVENTION

Definition of Terms

As used throughout this specification and the appended claims, the following terms have the following meanings:

The term "alkoxy" refers to an alkyl group appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" refers to a straight or branched chain hydrocarbon containing from 1 to 10 carbon atoms. Representative examples of alkyl include, but are not limited to, methyl, ethyl, n-propyl, iso-propyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "concurrently administering" or "concurrent administration" refers to administering, or the administration of, respectively, an α4β2 receptor ligand to a patient, who has been prescribed (or has consumed) at least one α4β2 PAM. This may mean simultaneous administration of an α4β2 PAM and an α4β2 receptor ligand, or administration of the medications at different times, but as part of the same therapy regimen.

The term "halo" or "halogen" refers to —Cl, —Br, —I or —F.

The term "nitrogen protecting group" refers to those groups intended to protect a nitrogen atom against undesirable reactions during synthetic procedures. Nitrogen protecting groups comprise carbamates, amides, N-benzyl derivatives, and imine derivatives. Preferred nitrogen protecting groups are acetyl, benzoyl, benzyl, benzyloxycarbonyl (Cbz), formyl, phenylsulfonyl, pivaloyl, tert-butoxycarbonyl (Boc), tert-butylacetyl, trifluoroacetyl, and triphenylmethyl (trityl). Nitrogen-protecting groups are appended onto primary or secondary amino groups by reacting the compound that contains the amine group with base, such as triethylamine, and a reagent selected from an alkyl halide, an alkyl triflate, a dialkyl anhydride, for example as represented by a dialkyl carbonate (alkyl-OC=O)$_2$O, a diaryl carbonate, for example as represented by (aryl-OC=O)$_2$O, an acyl halide, an alkylchloroformate, or an alkylsulfonylhalide, an arylsulfonylhalide, or halo-CON(alkyl)$_2$, for example acetylchloride, benzoylchloride, benzylbromide, benzyloxycarbonylchloride, formylfluoride, phenylsulfonylchloride, pivaloylchloride, (tert-butyl-O—C=O)$_2$O, trifluoroacetic anhydride, and triphenylmethylchloride.

The term "parenterally" refers to modes of administration, including intravenous, intramuscular, intraperitoneal, intrasternal, subcutaneous, intraarticular injection, and infusion.

The term "pharmaceutically acceptable carrier" refers to a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions; as well as other non-toxic compatible lubricants such as sodium lauryl sulfate and magnesium stearate; as well as coloring agents, releasing agents, coating agents, sweetening, flavoring and perfuming agents, preservatives and antioxidants can also be present in the composition, according to the judgment of one skilled in the art of formulations.

The term "pharmaceutically acceptable prodrug" or "prodrug" represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The term "pharmaceutically acceptable salts" includes salts and zwitterions of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use. Pharmaceutically acceptable salts are well-known in the art. The salts can be prepared in situ during the final isolation and purification of the compounds of the invention, or separately by reacting a free base function with a suitable organic acid.

Representative acid addition salts include, but are not limited to acetate, adipate, alginate, citrate, aspartate, benzoate, benzenesulfonate, bisulfate, butyrate, camphorate, camphorsulfonate, citrate, digluconate, ethanesulfonate, glycerophosphate, heptanoate, hexanoate, fumarate, hydrochloride, hydrobromide, hydroiodide, hydroxybutyrate, 2-hydroxyethanesulfonate (isethionate), lactate, malate, maleate, methanesulfonate, nicotinate, 2-naphthalenesulfonate, oxalate, pamoate, pectinate, persulfate, phenylacetate, 3-phenylpropionate, picrate, pivalate, propionate, salicylate, succinate, sulfate, tartrate, thiocyanate, phosphate, glutamate, carbonate, p-toluenesulfonate, and undecanoate.

Also, the basic nitrogen-containing groups can be quaternized with agents such as alkyl halides that include, but are not limited to, methyl, ethyl, propyl, butyl, decyl, lauryl, myristyl and stearyl chlorides, bromides and iodides; dialkyl sulfates such as dimethyl, diethyl, dibutyl and diamyl sulfates; arylalkyl halides such as benzyl and phenethyl bromides and others. Water or oil-soluble or dispersible products are thereby obtained.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the such. Other representative organic amines useful for the formation of base addition salts include ethylenediamine, ethanolamine, diethanolamine, piperidine, and piperazine.

The term "positive allosteric modulator" or PAM refers to a compound that enhances activity of an endogenous, or naturally occurring, ligand, such as but not limited to ACh, or an exogenously administered agonist. An asterisk is used herein to indicate that the exact subunit composition of a receptor is uncertain, for example α4β2* indicates a receptor that contains the α4 and β2 subunits proteins in combination with other subunits.

The phrase "therapeutically effective amount" of the compound of the invention refers to a sufficient amount of the compound to treat disorders, at a reasonable benefit/risk ratio applicable to any medical treatment.

Compounds of the Invention

Various embodiments of the invention can comprise compounds of formula (I) and pharmaceutically acceptable salts, isomers, and prodrugs thereof.

An embodiment of the invention is compounds having the formula (I)

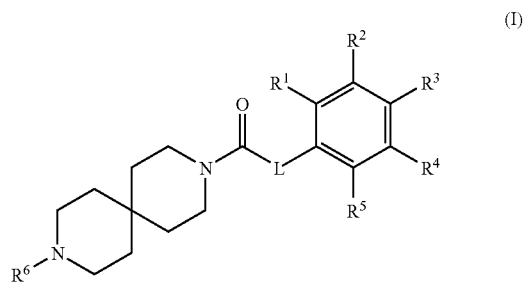

wherein L is a bond, $CH_2$, or $NR^7$; $R^1$, $R^2$, $R^3$, $R^4$ and $R^5$ are each independently selected from hydrogen, halogen, and methoxy, wherein at least one of $R^1$, $R^2$, $R^3$, $R^4$ and $R^5$ is halogen and at least one of $R^1$, $R^2$, $R^3$, $R^4$ and $R^5$ is methoxy; $R^6$ is hydrogen or methyl; and $R^7$ is hydrogen or alkyl.

In one embodiment of the invention, L is a bond.

In another embodiment of the invention, L is $CH_2$.

In a further embodiment of the invention, L is $NR^7$, wherein $R^7$ is hydrogen or alkyl.

In one embodiment, $R^2$ is methoxy and $R^3$ is halogen.

In another embodiment, $R^2$ is halogen and $R^3$ is methoxy.

In another embodiment, $R^2$ and $R^4$ are each halogen and $R^3$ is methoxy.

In another embodiment, $R^2$ is halogen and $R^3$ and $R^4$ are each methoxy.

In a further embodiment, $R^1$ and $R^3$ are each methoxy and $R^4$ is halogen.

In one embodiment, $R^6$ is hydrogen.

In another embodiment, $R^6$ is methyl.

Another embodiment of the invention is compounds of formula (II):

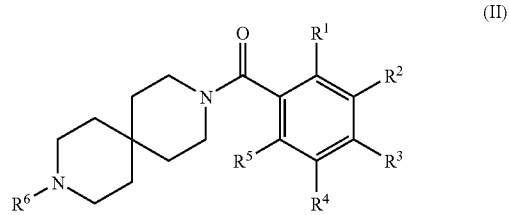

wherein $R^1$, $R^2$, $R^3$, $R^4$, $R^5$ and $R^6$ are as described for compounds of formula (I).

Another embodiment of the invention is compounds of formula (III):

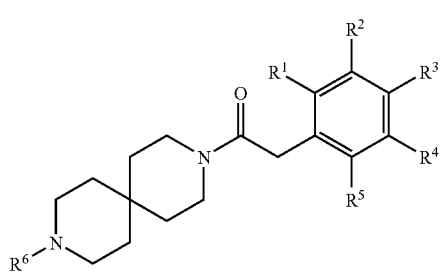

wherein $R^1$, $R^2$, $R^3$, $R^4$, $R^5$ and $R^6$ are as described for compounds of formula (I).

Another embodiment of the invention is compounds of formula (IV):

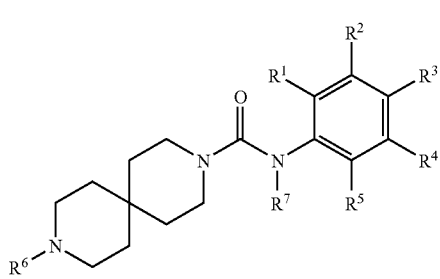

wherein $R^1$, $R^2$, $R^3$, $R^4$, $R^5$, $R^6$ and $R^7$ are as described for compounds of formula (I). In one embodiment, $R^7$ is hydrogen. In another embodiment, $R^7$ is alkyl.

Specific embodiments contemplated as part of the invention also include, but are not limited to, compounds of formula (I), as defined, for example:

3-(4-fluoro-3-methoxybenzoyl)-3,9-diazaspiro[5.5]undecane;
3-(4-fluoro-3-methoxybenzoyl)-9-methyl-3,9-diazaspiro[5.5]undecane;
3-(3-fluoro-4-methoxybenzoyl)-9-methyl-3,9-diazaspiro[5.5]undecane;
3-(3-chloro-4-methoxybenzoyl)-9-methyl-3,9-diazaspiro[5.5]undecane;
3-(3,5-dichloro-4-methoxybenzoyl)-9-methyl-3,9-diazaspiro[5.5]undecane;
3-(3-chloro-4,5-dimethoxybenzoyl)-9-methyl-3,9-diazaspiro[5.5]undecane;
N-(3-fluoro-4-methoxyphenyl)-9-methyl-3,9-diazaspiro[5.5]undecane-3-carboxamide;
N-(3-chloro-4-methoxyphenyl)-9-methyl-3,9-diazaspiro[5.5]undecane-3-carboxamide;
N-(5-chloro-2,4-dimethoxyphenyl)-9-methyl-3,9-diazaspiro[5.5]undecane-3-carboxamide; or
3-[(3-fluoro-4-methoxyphenyl)acetyl]-9-methyl-3,9-diazaspiro[5.5]undecane.

Compounds of the invention can exist in radiolabeled or isotope labeled form containing one or more atoms having an atomic mass or mass number different from the atomic mass or mass number most abundantly found in nature. Isotopes of atoms such as hydrogen, carbon, phosphorous, sulfur, fluorine, chlorine, and iodine include, but are not limited to, $^2H$, $^3H$, $^{14}C$, $^{32}P$, $^{35}S$, $^{18}F$, $^{36}Cl$, and $^{125}I$. Compounds that contain other radioisotopes of these and/or other atoms are within the scope of this invention. In an embodiment of the invention, the isotope-labeled compounds contain deuterium ($^2H$), tritium ($^3H$) or $^{14}C$ radioisotopes. Isotope and radiolabeled compounds of this invention can be prepared by the general methods well known to persons having ordinary skill in the art. Such isotope and radiolabeled compounds can be conveniently prepared by carrying out the procedures disclosed in the following Examples and Schemes by substituting a readily available isotope or radiolabeled reagent for a non-labeled reagent. The isotope and radiolabeled compounds of the invention may be used as standards to determine the effectiveness of α4β2 NNR ligands or modulators in the binding assays.

Within the present invention it is to be understood that compounds disclosed herein can exhibit the phenomenon of tautomerism. Thus, when the formulae drawings within this specification represent one of the possible tautomeric or stereoisomeric forms, it is to be understood that the invention encompasses any tautomeric or stereoisomeric form, and mixtures thereof, and is not to be limited merely to any one tautomeric or stereoisomeric form utilized within the naming of the compounds or formulae drawings.

Prodrugs

Prodrugs are pharmacologically inactive derivatives of an active drug designed to ameliorate some identified, undesirable physical or biological property. The physical properties are usually solubility (too much or not enough lipid or aqueous solubility) or stability related, while problematic biological properties include too rapid metabolism or poor bioavailability which itself may be related to a physicochemical property.

Prodrugs are usually prepared by: a) formation of ester, hemi esters, carbonate esters, nitrate esters, amides, hydroxamic acids, carbamates, imines, Mannich bases, and enamines of the active drug, b) functionalizing the drug with azo, glycoside, peptide, and ether functional groups, c) use of polymers, salts, complexes, phosphoramides, acetals, hemiacetals, and ketal forms of the drug. For example, see Andrejus Korolkovas's, "Essentials of Medicinal Chemistry", John Wiley-Interscience Publications, John Wiley and Sons, New York (1988), pp. 97-118, which is incorporated in its entirety by reference herein.

Methods of Preparing Compounds of the Invention

The compounds of the invention can be better understood in connection with the following synthetic schemes and methods, which illustrate a manner by which the compounds can be prepared.

Abbreviations which have been used in the descriptions of the schemes and the examples that follow are: O-(7-azabenzotriazol-1-yl)-N,N,N',N'-tetramethyluronium hexafluorophosphate (HATU), O-benzotriazol-1-yl-N,N,N',N'-tetramethyluronium tetrafluoroborate (TBTU), 2-(1H-benzo[d][1,2,3]triazol-1-yl)-1,1,3,3-tetramethylisouronium hexafluorophosphate(V) (HBTU), bis(2-oxo-3-oxazolidinyl) phosphinic chloride (BOPCl), 1-(3-dimethylaminopropyl)-3-ethylcarbodiimide hydrochloride (EDC or EDCI), (dimethylamino)pyridine (DMAP), high-pressure liquid chromatography (HPLC), 1-hydroxy-7-azabenzotriazole (HOAt), 1-hydroxybenzotriazole hydrate (HOBt), Dulbecco's Modified Eagle's Medium (DMEM), fetal bovine serum (FBS), N-methyl-D-glucamine (NMDG), and 4-(2-hydroxyethyl)-1-piperazineethanesulfonic acid (HEPES).

The compounds of this invention can be prepared according to the synthetic Scheme and/or Examples described. Representative procedures are shown in, but are not limited to, Schemes 1-3.

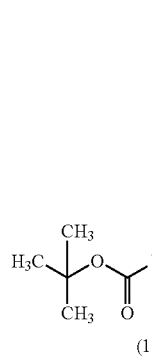
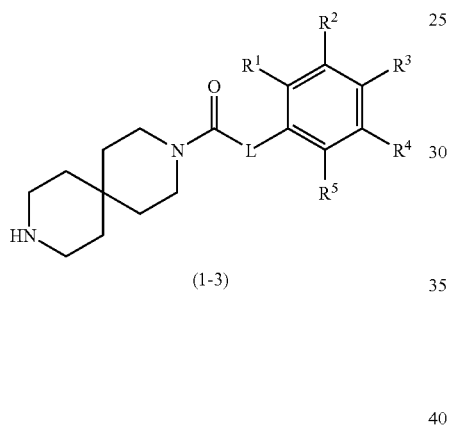

Compounds of formula (1-3) which are representative of compounds of formula (I) wherein L is a bond or $CH_2$ and $R^1$, $R^2$, $R^3$, $R^4$, and $R^5$ are as described for formula (I) are prepared by first reacting amine (1-1) with carboxylic acids of formula (1-2) under amide bond coupling conditions. Examples of conditions known to generate amides from a mixture of a carboxylic acid and an amine include but are not limited to adding a coupling reagent such as but not limited to N-(3-dimethylaminopropyl)-N'-ethylcarbodiimide (EDC or EDCI), 1,3-dicyclohexylcarbodiimide (DCC), bis(2-oxo-3-oxazolidinyl)phosphinic chloride (BOPCl), O-(7-azabenzotriazol-1-yl)-N,N,N',N'-tetramethyluronium hexafluorophosphate (HATU), O-benzotriazol-1-yl-N,N,N',N'-tetramethyluronium tetrafluoroborate (TBTU), and 2-(1H-benzo[d][1,2,3]triazol-1-yl)-1,1,3,3-tetramethylisouronium hexafluorophosphate(V) (HBTU). The coupling reagents may be added as a solid, a solution or as the reagent bound to a solid support resin. In addition to the coupling reagents, auxiliary-coupling reagents may facilitate the coupling reaction. Auxiliary coupling reagents that are often used in the coupling reactions include but are not limited to (dimethylamino)pyridine (DMAP), 1-hydroxy-7-azabenzotriazole (HOAt) and 1-hydroxybenzotriazole (HOBt). The reaction may be carried out optionally in the presence of a base such as triethylamine or diisopropylethylamine. The coupling reaction may be carried out in solvents such as but not limited to tetrahydrofuran, N,N,-dimethylformamide, dichloromethane, and ethyl acetate. The reaction may be conducted at ambient or elevated temperatures.

Alternatively, a compound of formula (1-1) can be reacted with a corresponding acid chloride of compounds of formula (1-2) either obtained from commercial sources or prepared by procedures known to one skilled in the art. Compounds of formula (1-2) may be treated with oxalyl chloride or thionyl chloride in a solvent such as dichloromethane or toluene at room temperature over to form the corresponding acid chloride. Subsequent treatment with (1-1) forms the desired amide bond. Elevated temperatures can be required to achieve complete reaction, and this can be realized in a solvent such as dichloroethane or toluene at temperatures of 30-100° C. Optionally an amine such as triethylamine or N,N-diisopropylethylamine can be added to the reaction mixture.

A second step in which the tert-butoxycarbonyl group is removed provides compounds of formula (1-3). The tert-butoxycarbonyl group can be treated with an acid such as hydrochloric acid or trifluoroacetic acid at room temperature in a solvent such as ether, dioxane, or dichloromethane to supply compounds of formula (1-3).

Compounds of formula (2-3) which are representative of compounds of formula (I) wherein L is a bond or $CH_2$ and $R^1$, $R^2$, $R^3$, $R^4$, and $R^5$ are as described for formula (I) are prepared by reacting amine (2-1) with carboxylic acids of formula (2-2) under amide bond coupling conditions described in Scheme 1. Alternatively, the carboxylic acid (2-2) can be transformed to the corresponding acid chloride and then reacted with amine (2-1) as described in Scheme 1 to give compounds of formula (2-3).

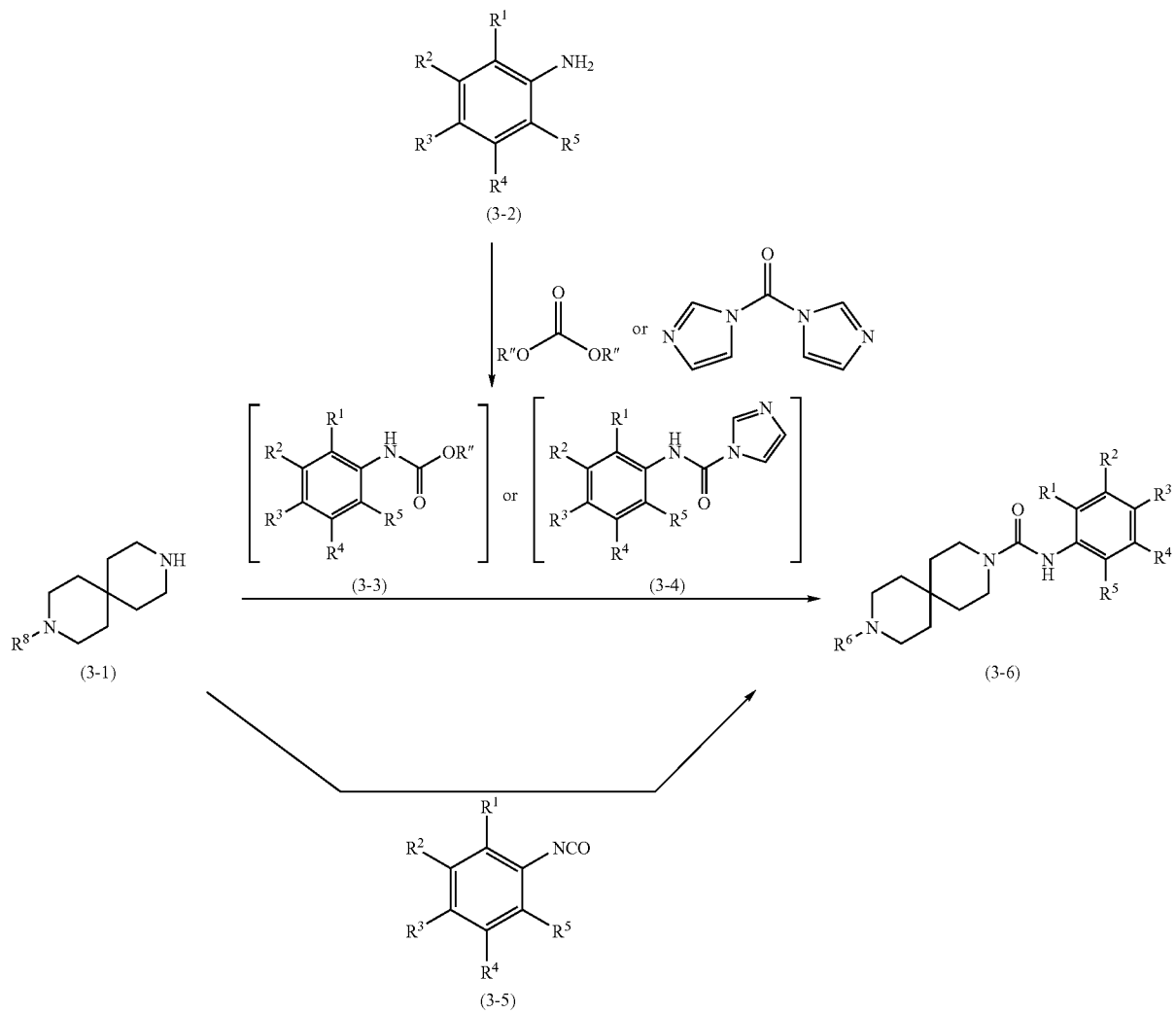

Scheme 3

Compounds of formula (3-6) which are representative of compounds of formula (I) and $R^1$, $R^2$, $R^3$, $R^4$, $R^5$, and $R^6$ are as described for formula (I) are prepared by reacting aniline (3-2) initially with a carbonate and subsequently by treating with amine (3-1), wherein $R^8$ is alkyl or a nitrogen protecting group such as but not limited to tert-butoxy carbonyl. The carbonate can be but is not limited to bis(2,5-dioxopyrrolidin-1-yl) carbonate or bis(2,4-dinitrophenyl) carbonate. The initial reaction can be conducted in solvents such as tetrahydrofuran, acetonitrile, or dichloromethane optionally in the presence of a base such as triethylamine, N,N-diisopropylethylamine, or pyridine at or near ambient temperature over a period of 1 to 24 hours. The intermediate (3-3) can then be reacted with amine (3-1) at or near room temperature in a solvent such as tetrahydrofuran, ethyl acetate, or dichloromethane optionally in the presence of a base such as triethylamine or N,N-diisopropylethylamine over a period of 2 to 24 hours. For those compounds wherein $R^8$ is a nitrogen protecting group, deprotection is further required to give compounds of formula (3-6) wherein $R^6$ is hydrogen. The deprotection step is dependent upon the particular protecting group used and is well within the skill of one in the art.

Alternatively, anilines of formula (3-2) can be reacted with 1,1'-carbonyldiimidazole optionally in the presence of a a base such as triethylamine or N,N-diisopropylethylamine in a solvent such as dichloromethane at 0-25° C. over 10 minutes to 8 hours. Intermediate (3-4) can then be treated with amine (3-1) over 1 to 24 hours. Removal of any protecting groups as described above provides compounds of formula (3-6).

Compounds of formula (3-6) can also be made in a one-step sequence. Amines of formula (3-1) can be reacted with isocyanates of formula (3-5) in a solvent such as but not limited to dichloromethane optionally in the presence of a base such as N,N-diisopropylethylamine at or near the reflux temperature over 2 to 24 hours. Removal of any protecting groups if required delivers compounds of formula (3-6) which are representative of a compounds of formula (I).

EXAMPLES

The compounds and processes of the invention will be better understood by reference to the following examples, which are intended as an illustration of and not a limitation upon the scope of the invention.

Example 1

3-(4-fluoro-3-methoxybenzoyl)-3,9-diazaspiro[5.5]undecane

Example 1A tert-butyl 9-(4-fluoro-3-methoxybenzoyl)-3,9-diazaspiro[5.5]undecane-3-carboxylate A solution of tert-butyl 3,9-diazaspiro[5.5]undecane-3-carboxylate (30 mg, 0.12 mmol; U.S. Pat. No. 5,451,578), 4-fluoro-3-methoxybenzoic acid (20 mg, 0.12 mmol; Aldrich), N,N-diisopropylethylamine (0.025 mL, 0.14 mmol), and O-(7-azabenzotriazol-1-yl)-N,N,N',N'-tetramethyluronium hexafluorophosphate (HATU; 54 mg, 0.14 mmol; Aldrich) in anhydrous N,N-dimethylformamide (1 mL) was stirred overnight at room temperature. The reaction was diluted with water (10 mL) and extracted with dichloromethane (2×10 mL). The combined organic extracts were dried over magnesium sulfate and concentrated in vacuo to provide the title compound which was carried on to the next step without further purification.

Example 1B

3-(4-fluoro-3-methoxybenzoyl)-3,9-diazaspiro[5.5]undecane

A solution of the product from Example 1A (48 mg, 0.12 mmol) was dissolved in dichloromethane (2 mL). Trifluoroacetic acid (0.19 mL, 1.2 mmol) was added to this solution. The reaction mixture was stirred at room temperature overnight. The reaction mixture was then diluted with water (10 mL) and extracted with dichloromethane (2×10 mL). The combined organic layers were dried over magnesium sulfate and concentrated in vacuo. The resulting oil was purified by reverse-phase HPLC (Waters XBridge C18 5 μm, 30×100 mm column, flow rate 40 mL/minute, 5-95% gradient of acetonitrile in 0.1% aqueous trifluoroacetic acid). Fractions containing the desired product were combined and concentrated under vacuum to afford the title compound as the trifluoroacetic acid salt: $^1$H NMR (300 MHz, methanol-$d_4$) δ ppm 1.51-1.72 (m, 4H), 1.72-1.86 (m, 4H), 3.14-3.24 (m, 4H), 3.42-3.54 (m, 2H), 3.64-3.76 (m, 2H), 3.90 (s, 3H), 6.97 (ddd, J=8.2, 4.3, 2.0 Hz, 1H), 7.14 (dd, J=8.1, 2.0 Hz, 1H), 7.17 (dd, J=11.0, 8.3 Hz, 1H); MS (DCI/NH$_3$) m/z 307 (M+H)$^+$.

Example 2

3-(4-fluoro-3-methoxybenzoyl)-9-methyl-3,9-diazaspiro[5.5]undecane

Example 2A

3-(4-fluoro-3-methoxybenzoyl)-9-methyl-3,9-diazaspiro[5.5]undecane trifluoroacetate A solution of 3-methyl-3,9-diazaspiro[5.5]undecane (50 mg, 0.30 mmol; Rice, L. M.; Grogan, C. H.; Freed, M. E. J. Heterocycl. Chem. 1964, 1, 125), 4-fluoro-3-methoxybenzoic acid (51 mg, 0.30 mmol; Aldrich), N,N-diisopropylethylamine (0.26 mL, 1.5 mmol), and O-(7-azabenzotriazol-1-yl)-N,N,N',N'-tetramethyluronium hexafluorophosphate (HATU; 169 mg, 0.446 mmol; Aldrich) in anhydrous N,N-dimethylformamide (1 mL) was stirred overnight at room temperature. The resulting material was directly purified by reverse-phase HPLC (Waters XBridge C18 5 μm, 30×100 mm column, flow rate 40 mL/minute, 5-95% gradient of acetonitrile in 0.1% aqueous trifluoroacetic acid) to afford the title compound as the trifluoroacetic acid salt: $^1$H NMR (300 MHz, methanol-$d_4$) δ ppm 1.38-1.85 (m, 6H), 1.98-2.12 (m, 2H), 2.88 (s, 3H), 3.04-3.25 (m, 2H), 3.34-3.52 (m, 4H), 3.65-3.82 (m, 2H), 3.90 (s, 3H), 6.97 (ddd, J=8.1, 4.1, 2.0 Hz, 1H), 7.14 (dd, J=8.1, 1.7 Hz, 1H), 7.17 (dd, J=11.2, 8.1 Hz, 1H); MS (DCI/NH$_3$) m/z 321 (M+H)$^+$.

Example 2B

3-(4-fluoro-3-methoxybenzoyl)-9-methyl-3,9-diazaspiro[5.5]undecane hydrochloride A solution of 4 M HCl in dioxane (0.146 mL, 0.584 mmol; Aldrich) was added dropwise to a vigorously stirred solution of the product of Example 2A (170 mg, 0.53 mmol) in ethyl acetate (10 mL). After 1 hour, the mixture was placed in a freezer overnight. The resulting solid material was collected by filtration and dried under vacuum to afford the title compound: $^1$H NMR (300 MHz, methanol-$d_4$) δ ppm 1.41-1.86 (m, 6H), 1.98-2.11 (m, 2H), 2.88 (s, 3H), 3.04-3.26 (m, 2H), 3.33-3.83 (m, 6H), 3.90 (s, 3H), 6.97 (ddd, J=8.2, 4.3, 1.8 Hz, 1H), 7.14 (dd, J=8.3, 2.0 Hz, 1H), 7.17 (dd, J=11.1, 8.3 Hz, 1H); MS (DCI/NH$_3$) m/z 321 (M+H)$^+$.

Example 3

3-(3-fluoro-4-methoxybenzoyl)-9-methyl-3,9-diazaspiro[5.5]undecane

A solution of 3-fluoro-4-methoxybenzoic acid (35 mg, 0.99 mmol; Aldrich), N,N-diisopropylethylamine (0.72 mL, 0.42 mmol), N-(3-dimethylaminopropyl)-N'-ethylcarbodiimide hydrochloride (EDC; 48 mg, 0.25 mmol; Aldrich), and 1-hydroxybenzotriazole hydrate (HOBt; 38 mg, 0.25 mmol; Aldrich) in anhydrous N,N-dimethylformamide (1 mL) was stirred for 30 minutes at room temperature, and then 3-methyl-3,9-diazaspiro[5.5]undecane dihydrochloride (50 mg, 0.21 mmol; Rice, L. M.; Grogan, C. H.; Freed, M. E. J. Heterocycl. Chem. 1964, 1, 125) was added and stirring was continued overnight. The resulting solution was diluted with methanol and purified by reverse-phase HPLC (Waters XBridge C18 5 μm, 30×100 mm column, flow rate 40 mL/minute, 5-95% gradient of acetonitrile in 0.1% aqueous trifluoroacetic acid) to afford the title compound as the trifluoroacetic acid salt: $^1$H NMR (300 MHz, methanol-$d_4$) δ ppm 1.45-1.54 (m, 2H), 1.54-1.70 (m, 2H), 1.68-1.81 (m, 2H), 1.97-2.11 (m, 2H), 2.88 (s, 3H), 3.05-3.22 (m, 4H), 3.33-3.77 (m, 4H), 3.91 (s, 3H), 7.16 (t, J=8.5 Hz, 1H), 7.18-7.20 (m, 1H), 7.21 (d, J=8.5 Hz, 1H); MS (DCI/NH$_3$) m/z 321 (M+H)$^+$.

Example 4

3-(3-chloro-4-methoxybenzoyl)-9-methyl-3,9-diazaspiro[5.5]undecane

A solution of 3-methyl-3,9-diazaspiro[5.5]undecane (50 mg, 0.30 mmol; Rice, L. M.; Grogan, C. H.; Freed, M. E. J. Heterocycl. Chem. 1964, 1, 125), 3-chloro-4-methoxybenzoic acid (55 mg, 0.30 mmol; Aldrich), and N,N-diisopropylethylamine (0.052 mL, 0.30 mmol) in anhydrous N,N-dimethylformamide (1 mL) was treated with O-(7-azabenzotriazol-1-yl)-N,N,N',N'-tetramethyluronium hexafluorophosphate (HATU; 113 mg, 0.30 mmol; Aldrich) and the mixture was stirred overnight at room temperature. The resulting solution was diluted with methanol and purified by reverse-phase HPLC (Waters XBridge C18 5 μm, 30×100 mm column, flow rate 40 mL/minute, 5-95% gradient of acetonitrile in 0.1% aqueous trifluoroacetic acid) to afford the title compound as the trifluoroacetic acid salt: $^1$H NMR (300 MHz, methanol-$d_4$) δ ppm 1.43-1.55 (m, 2H), 1.55-1.69 (m, 2H), 1.70-1.79 (m, 2H), 2.04 (m, 2H), 2.88 (s, 3H), 3.03-3.23 (m, 2H), 3.35-3.43 (m, 2H), 3.46-3.74 (m, 4H), 3.93 (s, 3H), 7.14 (d, J=8.5 Hz, 1H), 7.36 (dd, J=8.5, 2.0 Hz, 1H), 7.46 (d, J=2.0 Hz, 1H); MS (DCI/NH$_3$) m/z 337 (M+H)$^+$.

Example 5

3-(3,5-dichloro-4-methoxybenzoyl)-9-methyl-3,9-diazaspiro[5.5]undecane

A solution of 3-methyl-3,9-diazaspiro[5.5]undecane (50 mg, 0.30 mmol; Rice, L. M.; Grogan, C. H.; Freed, M. E. *J. Heterocycl. Chem.* 1964, 1, 125), 3,5-dichloro-4-methoxybenzoic acid (66 mg, 0.30 mmol), and N,N-diisopropylethylamine (0.052 mL, 0.30 mmol) in anhydrous N,N-dimethylformamide (1 mL) was treated with O-(7-azabenzotriazol-1-yl)-N,N,N',N'-tetramethyluronium hexafluorophosphate (HATU; 113 mg, 0.30 mmol; Aldrich) and the mixture was stirred overnight at room temperature. The resulting solution was diluted with methanol and purified by reverse-phase HPLC (Waters XBridge C18 5 μm, 30×100 mm column, flow rate 40 mL/minute, 5-95% gradient of acetonitrile in 0.1% aqueous trifluoroacetic acid) to afford the title compound as the trifluoroacetic acid salt: $^1$H NMR (300 MHz, methanol-$d_4$) δ ppm 1.43-1.55 (m, 2H), 1.55-1.69 (m, 2H), 1.70-1.79 (m, 2 H), 2.04 (m, 2H), 2.88 (s, 3H), 3.03-3.23 (m, 2H), 3.35-3.43 (m, 2H), 3.46-3.74 (m, 4H), 3.92 (s, 3H), 7.46 (s, 2H); MS (DCI/NH$_3$) m/z 371 (M+H)$^+$.

Example 6

3-(3-chloro-4,5-dimethoxybenzoyl)-9-methyl-3,9-diazaspiro[5.5]undecane

A solution of 3-methyl-3,9-diazaspiro[5.5]undecane (50 mg, 0.30 mmol; Rice, L. M.; Grogan, C. H.; Freed, M. E. *J. Heterocycl. Chem.* 1964, 1, 125), 3-chloro-4,5-dimethoxybenzoic acid (65 mg, 0.30 mmol; Aldrich), and N,N-diisopropylethylamine (0.052 mL, 0.30 mmol) in anhydrous N,N-dimethylformamide (1 mL) was treated with O-(7-azabenzotriazol-1-yl)-N,N,N',N'-tetramethyluronium hexafluorophosphate (HATU; 113 mg, 0.30 mmol; Aldrich) and the mixture was stirred overnight at room temperature. The resulting solution was diluted with methanol and purified by reverse-phase HPLC (Waters XBridge C18 5 μm, 30×100 mm column, flow rate 40 mL/minute, 5-95% gradient of acetonitrile in 0.1% aqueous trifluoroacetic acid) to afford the title compound as the trifluoroacetic acid salt: $^1$H NMR (300 MHz, methanol-$d_4$) δ ppm 1.40-1.58 (m, 2H), 1.57-1.67 (m, 2H), 1.71-1.86 (m, 2H), 1.97-2.11 (m, 2H), 2.88 (s, 3H), 3.10-3.23 (m, 2H), 3.33-3.42 (m, 2H), 3.43-3.51 (m, 2H), 3.63-3.79 (m, 2H), 3.85 (s, 3H), 3.89 (s, 3H), 7.00 (d, J=1.7 Hz, 1H), 7.04 (d, J=1.7 Hz, 1H); MS (DCI/NH$_3$) m/z 367 (M+H)$^+$.

Example 7

N-(3-fluoro-4-methoxyphenyl)-9-methyl-3,9-diazaspiro[5.5]undecane-3-carboxamide

To a suspension of bis(2,5-dioxopyrrolidin-1-yl) carbonate (1.25 equiv; NovaBiochem) in anhydrous acetonitrile (2.5 M) was added a solution of 3-fluoro-4-methoxyaniline (1.25 equivalents; Aldrich) and pyridine (1.3 equivalents) in acetonitrile (0.25 M). The mixture was stirred at room temperature overnight. A solution of 3-methyl-3,9-diazaspiro[5.5]undecane (1.0 equivalent; Rice, L. M.; Grogan, C. H.; Freed, M. E. *J. Heterocycl. Chem.* 1964, 1, 125) in tetrahydrofuran (0.5 M) was added, followed by diisopropylethylamine (2 equivalents). The suspension was stirred at room temperature overnight, concentrated, and purified by reverse-phase HPLC (C18, 0-95% gradient of acetonitrile/0.1% trifluoroacetic acid) to provide the title compound as the trifluoroacetate salt: $^1$H NMR (300 MHz, methanol-$d_4$) δ ppm 1.46-1.54 (m, 2H), 1.54-1.69 (m, 2H), 1.69-1.76 (m, 2H), 1.96-2.07 (m, 2H), 2.88 (s, 3H), 3.08-3.22 (m, 2H), 3.33-3.44 (m, 2H), 3.46-3.57 (m, 4H), 3.83 (s, 3H), 6.96 (dd, J=9.0, 9.0 Hz, 1H), 7.02 (dd, J=9.0, 2.3 Hz, 1H), 7.20 (dd, J=13.2, 2.2 Hz, 1H); MS (ESI+) m/z 336 (M+H)$^+$.

Example 8

N-(3-chloro-4-methoxyphenyl)-9-methyl-3,9-diazaspiro[5.5]undecane-3-carboxamide

A mixture of 3-methyl-3,9-diazaspiro[5.5]undecane (100 mg, 1.0 equivalent; Rice, L. M.; Grogan, C. H.; Freed, M. E. *J. Heterocycl. Chem.* 1964, 1, 125), 2-chloro-4-isocyanato-1-methoxybenzene (1.01 equivalents; Aldrich), and N,N-diisopropylethylamine (2 equivalents) in anhydrous dichloromethane (3 mL) was heated to reflux overnight. After cooling, the mixture was washed with saturated aqueous sodium bicarbonate and water, dried over magnesium sulfate, and concentrated. The residue was purified by reverse-phase HPLC (C18, acetonitrile/0.1% trifluoroacetic acid) to afford the title compound as the trifluoroacetic acid salt: $^1$H NMR (300 MHz, CDCl$_3$) δ ppm 1.57-1.67 (m, 4H), 1.83-1.96 (m, 4H), 2.20-2.30 (m, 4H), 2.80-2.85 (m, 3H), 3.40-3.53 (m, 4H), 3.87 (s, 3H), 6.29 (s, 1H), 6.86 (d, 1H), 7.16 (dd, J=7 Hz, 1H), 7.28 (d, J=7 Hz, 1H); MS (ESI+) m/z 352 (M+H)$^+$.

Example 9

N-(5-chloro-2,4-dimethoxyphenyl)-9-methyl-3,9-diazaspiro[5.5]undecane-3-carboxamide A mixture of 3-methyl-3,9-diazaspiro[5.5]undecane (100 mg, 1.0 equiv; Rice, L. M.; Grogan, C. H.; Freed, M. E. *J. Heterocycl. Chem.* 1964, 1, 125), 1-chloro-5-isocyanato-2,4-dimethoxybenzene (1.01 equivalents; Aldrich), and N,N-diisopropylethylamine (2 equivalents) in anhydrous dichloromethane (3 mL) was heated to reflux overnight. After cooling, the mixture was washed with saturated sodium bicarbonate and water, dried over magnesium sulfate, and concentrated. The residue was purified by reverse-phase HPLC (C18, acetonitrile/0.1% trifluoroacetic acid) to afford the title compound as the trifluoroacetic acid salt: $^1$H NMR (300 MHz, CDCl$_3$) δ ppm 1.57-1.67 (m, 3H), 1.83-1.95 (m, 4H), 2.48-2.50 (m, 5H), 2.80-2.85 (m, 3H), 3.41-3.51 (m, 4H), 3.88 (s, 3H), 3.89 (s, 3H), 6.51 (s, 1H), 6.79 (bs, 1H), 8.11 (s, 1H); MS (ESI+) m/z 382 (M+H)$^+$.

Example 10

3-[(3-fluoro-4-methoxyphenyl)acetyl]-9-methyl-3,9-diazaspiro[5.5]undecane

A mixture of 3-methyl-3,9-diazaspiro[5.5]undecane (100 mg, 1.0 equivalent; Rice, L. M.; Grogan, C. H.; Freed, M. E.

*J. Heterocycl. Chem.* 1964, 1, 125), 2-(3-fluoro-4-methoxyphenyl)acetic acid (1.01 equiv; Fluka), and N,N-diisopropylethylamine (4 equivalents) in anhydrous N,N-dimethylformamide (1 mL) was treated with O-azabenzotriazol-1-yl)-N,N,N',N'-tetramethyluronium hexafluorophosphate (HATU; 1.5 equiv; Aldrich) at room temperature overnight. The mixture was concentrated under reduced pressure and the residue was purified by reverse-phase HPLC(C18, acetonitrile/0.1% trifluoroacetic acid) to afford the title compound as the trifluoroacetic acid salt: $^1$H NMR (300 MHz, CDCl$_3$) δ ppm 1.35-2.03 (m, 12H), 2.75-2.85 (m, 3H), 3.39-3.65 (m, 4H), 3.70 (s, 2H), 3.88 (s, 3H), 6.90-7.01 (m, 3H); MS (ESI+) m/z 335 (M+H)$^+$.

Compositions of the Invention

Another embodiment of the invention provides pharmaceutical compositions comprising a therapeutically effective amount of a compound of formula (I) in combination with a pharmaceutically acceptable carrier. The compositions comprise compounds of the invention formulated together with one or more non-toxic pharmaceutically acceptable carriers.

Another embodiment of the invention provides pharmaceutical compositions, comprising:
(i) a nicotinic receptor ligand,
(ii) an α4β2 PAM, and
(iii) at least one pharmaceutically acceptable carrier or excipient.

Another embodiment of the invention provides pharmaceutical compositions, comprising:
(i) a nicotinic receptor ligand,
(ii) the compound of formula (I), and
(iii) at least one pharmaceutically acceptable carrier or excipient.

The pharmaceutical compositions can be formulated for oral administration in solid or liquid form, for parenteral injection or for rectal administration.

The pharmaceutical compositions of this embodiment of the invention can be administered to humans and other mammals orally, rectally, parenterally, intracisternally, intravaginally, intraperitoneally, topically (as by powders, ointments or drops), buccally or as an oral or nasal spray.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions can also contain adjuvants such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It also can be desirable to include isotonic agents, for example, sugars, sodium chloride and the like. Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug can depend upon its rate of dissolution, which, in turn, may depend upon crystal size and crystalline form. Alternatively, a parenterally administered drug form can be administered by dissolving or suspending the drug in an oil vehicle.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions can be formulated according to the known art using suitable dispersing or wetting agents and suspending agents. The sterile injectable preparation also can be a sterile injectable solution, suspension or emulsion in a nontoxic, parenterally acceptable diluent or solvent such as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well-known in the pharmaceutical formulating art. They can optionally contain opacifying agents and can also be of a composition that they release the active ingredient(s) only, or preferentially, in a certain part of the intestinal tract in a delayed manner. Examples of materials useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vagina and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, eardrops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention also can be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also contemplated as being within the scope of this invention. Aqueous liquid compositions of the invention also are particularly useful.

The compounds of the invention can be used in the form of pharmaceutically acceptable salts derived from inorganic or organic acids.

Methods of Use

The biological effects of the compounds of the invention result from positive allosteric modulation of an α4β2 subtype of nicotinic acetylcholine receptor. Representative compounds of the invention, represented by Examples 1-10, demonstrate α4β2 NNR PAM activity. As such, compounds and compositions of the invention are useful for the treatment of conditions and disorders related to cholinergic dysfunction and for conditions and disorders responsive to the action of NNR modulators. The method is useful for treating, preventing or both treating and preventing conditions and disorders related to α4β2 NNR PAM activity, particularly in mammals.

More particularly, the method is useful for conditions and disorders related to attention deficit disorder, attention deficit hyperactivity disorder (ADHD), Alzheimer's disease (AD), schizophrenia, mild cognitive impairment, age-associated memory impairment (AAMI), senile dementia, AIDS dementia, Pick's disease, Parkinson's disease, Tourette's syndrome, dementia associated with Lewy bodies, dementia associated with Down's syndrome, schizophrenia, smoking cessation, or nicotine withdrawal syndrome, substance abuse such as alcohol abuse and nicotine abuse, amyotrophic lateral sclerosis (ALS), Huntington's disease, depression, acute pain, post-surgical pain, chronic pain, inflammatory pain, and neuropathic pain. The method is useful for conditions and disorders characterized by neuropyschological and cognitive dysfunction, for example in Alzheimer's disease, bipolar disorder, schizophrenia, schizoaffective disorder, and other related disorders characterized by neuropyschological and cognitive dysfunction, in particular.

Compounds of the invention also are useful for treating, preventing or both treating and preventing pain, particularly in mammals. Administration of compounds of the invention is useful for treating nociceptive and neuropathic forms of pain, for example, chronic pain, analgesic pain, post-surgical pain, neuropathic pain, and diabetic neuropathy. Such compounds are particularly beneficial for reducing adverse ganglionic effects such as at gastrointestinal systems (e.g. emesis) and for enhancing the effects of NNR ligands in such treatment.

A further aspect of the invention relates to a method of selectively modulating NNR activity, for example α4β2 NNR PAM activity, in combination with a nicotinic agonist or partial agonist to improve the tolerability of therapy using such nicotinic agonist or partial agonist, which is further described herein below. When dosed in combination with NNR agonists, such compounds could enhance efficacy in various disease states including pain and cognitive deficits by preferentially modulating α4β2 activity, and enabling improved separation from potential adverse emesis, cardiovascular and other effects.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in a pharmaceutically acceptable salt. Alternatively, the compound can be administered as a pharmaceutical composition containing the compound of interest in combination with one or more pharmaceutically acceptable carriers. The phrase "therapeutically effective amount" of the compound of the invention refers to a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or animal ranges from about 0.010 mg/kg body weight to about 500 mg/kg body weight. More preferable doses can be in the range of from about 0.010 mg/kg body weight to about 50 mg/kg body weight. If desired, the effective daily dose can be divided into multiple doses for purposes of administration. Consequently, single dose compositions may contain such amounts or submultiples thereof to make up the daily dose. When co-administered with other nicotinic ligands (agonist, partial agonists), the dose ranges of the compounds of this invention may be adjusted to achieve desirable efficacy and tolerability profiles.
Use with Neuronal Nicotinic Acetylcholine Receptor Ligands It has been found that the efficacy of nicotinic receptor ligands can be improved by combining the nicotinic receptor ligand, particularly an α4β2 receptor ligand (agonist, partial agonist), with compounds of the invention, i.e. a nicotinic acetylcholine receptor α4β2 subtype selective PAM. Such combinations are highly efficient for improving the efficacy of α4β2 ligand for treatment of pain and other disease indications such as cognitive deficits when compared to administration of an α4β2 receptor ligand alone.

Nicotinic acetylcholine ligands modulate the function by altering the activity of the receptor. Suitable compounds also can be partial agonists that partially block or partially activate the α4β2 receptor or agonists that activate the receptor. PAMs are compounds that potentiate receptor responses to acetylcholine without themselves triggering receptor activation or desensitization, or either, of the receptor. Nicotinic acetylcholine receptor α4β2 receptor ligands suitable for the invention can include full agonists or partial agonists, and can exhibit varying degrees of selectivity towards the α4β2 receptor.

One manner for identifying suitable agonists of the α4β2 receptor is by assessing $K_i$ values for the displacement of [$^3$H]-cytisine binding. Typical ligands can have $K_i$ values ranging from 1 μM to 10 μM. The [$^3$H]-cytisine binding assays have been well reported; however, further details for carrying out the assays can be obtained in International Publication No. WO 99/32480; U.S. Pat. Nos. 5,948,793 and 5,914,328; International Publication No. WO 2001/081347; U.S. Pat. No. 6,809,105; International Publication No. WO 00/71534; and U.S. Pat. No. 6,833,370.

Accordingly, α4β2 receptor ligands suitable for the invention can be compounds of various chemical classes. Particularly, some examples of α4β2 receptor ligands suitable for the invention include, but are not limited to, heterocyclic ethers, N-substituted diazabicycles, and heterocyclic substituted amino azacycles (see International Publication No. WO 99/32480, published Jul. 1, 1999; U.S. Pat. No. 5,948,793, issued Sep. 7, 1999; U.S. Pat. No. 5,914,328, issued Jun. 22, 1999; International Publication No. WO 2001/081347, published Sep. 23, 2004; U.S. Pat. No. 6,809,105, issued Oct. 26, 2004; International Publication No. WO 00/71534, published Nov. 30, 2000; U.S. Pat. No. 6,833,370, issued Dec. 21, 2004; all of which are hereby incorporated by reference in their entirety). Further description and methods for preparing the compounds have been reported in patents, patent publications, and international patent publications cited.

Various forms of pain, psychiatric and neurological disorders can be treated by concurrently administering to a patient (i.e. a human) in need thereof, an α4β2 PAM and an α4β2 receptor ligand. Such combination may be especially useful in expanding the dosage range for obtaining therapeutically beneficial effects.

Establishing such a proper dosing schedule will be readily apparent to one skilled in the art, such as a physician treating various pain states.

The dosage range at which the α4β2 PAM and an α4β2 receptor ligand will be administered concurrently can vary widely. The specific dosage will be chosen by the patient's physician taking into account the particular compounds chosen, the severity of the patient's illness, any other medical conditions or diseases the patient is suffering from, other drugs the patient is taking and their potential to cause an interaction or adverse event, the patient's previous response to medication, and other factors.

The α4β2 PAM and an α4β2 receptor ligand should be administered concurrently in amounts that are effective to treat the patient's pain, cognitive disorder, or related condition. In more general terms, one would create a combination of the present invention by choosing a dosage of an α4β2 PAM and an α4β2 receptor ligand according to the spirit of the guidelines presented above.

In another embodiment of the invention, the method is carried out by administering an α4β2 PAM together with an α4β2 receptor ligand in any manner which provides effective levels of the compounds in the body at the same time.

In another embodiment of the invention, the method is carried out by administering an α4β2 PAM selected from Examples 1-10 described herein, together with an α4β2 receptor ligand in any manner which provides effective levels of the compounds in the body at the same time.

Various embodiments of the invention can be administered to humans and other mammals orally, rectally, parenterally, intracisternally, intravaginally, intraperitoneally, topically (as by powders, ointments or drops), bucally or as an oral or nasal spray. Various embodiments of the invention should be construed to cover any route of administration that is appropriate for the medications involved and for the patient. For example, transdermal administration may be very desirable for patients who are forgetful or petulant about taking oral medicine. Injections may be appropriate for patients refusing their medication. One of the drugs may be administered by one route, such as oral, and the others may be administered by the transdermal, percutaneous, intravenous, intramuscular, intranasal, intrarectal or intravaginal route, in particular circumstances. The route of administration may be varied in any way, limited by the physical properties of the drugs and the convenience of the patient and the caregiver.

Combination Use in Pain Therapy

Based on the diversity of the mechanisms underlying chronic pain (e.g. nociceptive or neuropathic, degrees of pain intensity, various etiologies, etc.), currently available pain medications are not efficacious in all patients or in all pain conditions. Analgesics can be broadly categorized as non-opioid analgesics (acetaminophen and non-steroidal anti-inflammatory drugs (NSAIDs)), opioid analgesics (morphine) and adjuvant analgesics or co-analgesics (antiepileptic drugs and antidepressants). In a simplified classification, non-opioid analgesics are mostly used to relieve mild to moderate nociceptive pain, adjuvant analgesics (gabapentin, pregabalin) are used to relieve neuropathic pain, and opioid analgesics are used to treat severe pain of all origins, depending on the dose prescribed.

NNR ligands act at multiple locations throughout the pain pathway to relieve pain. NNRs are found on primary sensory neurons (periphery) where nociceptive information is initiated, in the cell body regions of these neurons (i.e. the dorsal root ganglion or DRG), the dorsal spinal cord where the first pain synapse is located, in the brainstem cell body regions that control descending innervation, as well as in the higher brain regions that integrate and perceive sensory information such as the thalamus and the cortex. The current theory supported by evidence from multiple sources (reviewed in Decker et al., *Curr. Topics Med. Chem.,* 4: 369, 2004) is that anti-nociceptive effects of NNR ligands are mediated by activation of brain stem nuclei with descending inhibitory inputs to the spinal cord. Additional pathways may also mediate analgesic effects of NNR agonists in persistent or neuropathic pain.

One other aspect of the invention is the potential to enhance efficacy of other medications used for treating pain. As noted above, examples of currently used drugs include opioids, gabapentin, pregabalin, duloxetine and others. Novel mechanisms such as cannabinoids, vanilloid receptor antagonists and sodium channel blockers are also being developed for the treatment of pain. For many of these mechanisms, it is emerging that a component of efficacy may be driven by activation of descending inhibitory inputs. For example, opioid analgesics can block pain transmission, in part by increasing descending inhibitory pathways to modulate pain transmission at the spinal level (Pasternack, G. W., *Clin. Neurophar-macol.* 16: 1, 1993; Lauretti, G. T., *Expert Reviews in Neurotherapeutics,* 6: 613-622, 2006). Since these drugs exert their effect via activating descending inhibitory inputs, and these pathways can be shared or commonly activated by α4β2 NNR ligands, it is anticipated that co-administration of compounds of the invention, as α4β2 selective PAMs, can lead to enhanced efficacy of other analgesic agents by amplifying the descending inhibitory control of spinal cord activation. Thus, combining compounds of the invention with such therapeutic agents for pain affords the opportunity to create analgesic medications with either a broader or superior spectrum of efficacy that would improve the treatment of chronic pain.

Accordingly, another embodiment of the invention is a method for use in treating or preventing pain, including neuropathic pain and cognitive disorders in a patient in need thereof, comprising:
  (i) administering an amount of neuronal nicotinic receptor ligand to the patient; and
  (ii) administering an amount of the compound of formula (I) to the patient, wherein the amounts of (i) and (ii) together are more effective in treating pain or cognitive disorders.

Another embodiment of the invention is a method for use in treating or preventing pain in a patient in need thereof, comprising:
  (i) administering an amount of the compound of formula (I) to the patient; and
  (ii) administering a pain medication comprising a compound selected from an opioid, gabapentin, pregabalin, duloxetine, a cannabinoid ligand, a vanilloid receptor antagonist, and a sodium channel blocker wherein a descending modulatory pathway that is shared or commonly activated via the α4β2 nicotinic receptor mechanism is activated.

Determination of Biological Activity

One manner to characterize α4β2 PAM activity is by characterization in clonal cell lines (for example, human embryonic kidney 293 cells) expressing the human neuronal nicotinic acetylcholine receptor subtype α4β2, particularly by use of Fluorescent Image Plate Reader technology. Effects on calcium flux or membrane potential changes can be assessed. Such assays have been reported and further details for carrying out the assays can be obtained in International Publication No. WO 2006/114400. Another method to identify and characterize allosteric modulator activity is by expressing the α4β2 subunits in *Xenopus* oocytes, and by measuring electrophysiological effects on ligand-evoked current responses as previously described in Curtis, L., et al., *Molecular Pharmacology,* 61: 127-135, 2002.

To determine the effectiveness of representative compounds of this invention as ligands for α4β2 PAM activity, the compounds of the invention can be evaluated according to the Calcium Flux Assay described below.

Drugs that block the cardiac potassium channel encoded by the human ether-a-go-go gene (hERG) have been associated clinically with QT interval prolongation, proarrhythmia, and in some rare cases, sudden cardiac death. The identification of drugs that block hERG has become a critical component of the safety profile. The [$^3$H]dofetilide/HEK-293 membrane competition binding assay described below permits the ranking of compounds for their potential to block the hERG potassium channel.

Calcium Flux Assays using Cells Expressing NNR Subtypes

Human embryonic kidney (HEK) 293 cells stably expressing human α4β2 or α3β4 combinations are grown to confluency in 162 cm² tissue culture flasks in DMEM media supplemented with 10% FBS and 25 µg/mL zeocin and 200 µg/mL hygromycin B. Cells expressing rat or ferret subunits may also be used. For assessing α3* or α7* selectivity, IMR-32 cells may also be used. IMR-32 neuroblastoma cells (ATCC) are grown to confluency in 162 cm² tissue culture flasks in minimum essential media supplemented with 10% FBS and 1 mM sodium pyruvate, 1% non-essential amino acids and 1% antibiotic-antimycotic. For the calcium flux assay, the cells are then dissociated using cell dissociation buffer and 100-150 µL per well of 3.5×10⁵ cells/mL cell suspension (~50,000-100,000 cells/well) was plated into 96-well black plates (poly-D-lysine precoated) with clear bottom and maintained for 24-48 hours in a tissue culture incubator at 37° C. under an atmosphere of 5% $CO_2$: 95% air. Other clonal cell lines or primary cell cultures that express endogenous α4* nicotinic receptors may also be used in this assay. Calcium flux was measured using calcium-3 assay kit (Molecular Devices, Sunnyvale, Calif.) or fluo-4 (Invitrogen). A stock solution of the dye was prepared by dissolving each vial supplied by the vendor in Hank's balanced salt solution buffer (HBSS) or 150 mM NMDG, 20 mM calcium chloride containing 10 mM HEPES. The stock solution was diluted 1:20 using the same buffer before use. The growth media was removed from the cells. The cells were loaded with 100 µL of the dye per well and incubated at room temperature for up to one hour for HEK 293 clonal stable cell lines or 30 minutes-45 minutes at 37° C. for IMR-32 cells. Fluorescence measurements were read simultaneously from all the wells by a Fluorometic Imaging Plate Reader (FLIPR) at an excitation wavelength of 480 nm and an emission wavelength of 520 nm. Baseline fluorescence was measured for the first 6 seconds at which 3× concentrations of modulator/test compounds were added to the cell plate at 50 µL and incubated for five minutes. The fluorescence intensity was captured every second for the first 1 minute followed by every 5 seconds for an additional 4 minutes. This procedure was followed by 50 µL of 4× concentration of agonist and readings were taken for a period of 3-5 minutes as described above.

The ability of test compounds to positively modulate the response (i.e., increase the response) induced by a submaximal concentration of agonist ($EC_{20-30}$%) such as nicotine is measured. Potentiation is measured based on peak fluorescence responses by screening compounds at fixed concentrations or in a concentration-response manner to derive $EC_{50}$ values. The concentration dependence of changes in fluorescence responses is fitted by nonlinear regression analysis (GraphPad Prism, San Diego, Calif.) to obtain $EC_{50}$ values. The degree of potentiation and $EC_{50}$ values of the test compounds are typically calculated. To enable rank ordering of potency and efficacy, data may be normalized to a reference PAM. In general, compounds of the invention selectively potentiate α4β2 NNRs, but not others including ganglionic receptors expressed in IMR-32 cells. At α4β2 receptors, compounds of the invention typically increase fluorescence responses to submaximal nicotine (considered as 100%) to values ranging from 120 to 500%. The $EC_{50}$ values of active compounds were determined by concentration response analysis ($EC_{50}$) range from about 10 nM to about 100 µM. The data demonstrate the compounds of the invention are α4β2 PAMs that potentiate receptor responses to acetylcholine without themselves triggering receptor activation or desensitization, or either, of the receptor.

Table 1 lists the results for representative compounds of the present invention.

TABLE 1

Examples of Selected α4β2 PAMs

| Example No. | $EC_{50}$ (µM) |
|---|---|
| 2 | 0.97 |
| 3 | 4.30 |
| 4 | 0.16 |
| 5 | 0.04 |
| 6 | 0.36 |
| 7 | 1.62 |
| 8 | 0.61 |
| 9 | 3.74 |
| 10 | 1.69 |

[³H]dofetilide/HEK-293 Membrane Competition Binding Assay

The binding affinity of test drugs for the hERG cardiac potassium channel was determined by their ability to displace tritiated dofetilide (a class III antiarrhythmic drug and potent hERG blocker) in membrane homogenates from HEK-293 cells heterogously expressing the hERG channel. The assay was performed as previously described (Diaz, G.; Daniell, K.; Leitza, S. T.; Martin, R. L.; Su, Z.; McDermott, J. S.; Cox, B. F.; Gintant, G. A. The [³H]dofetilide binding assay is a predictive screening tool for hERG blockade and proarrhythmia: Comparison of intact cell and membrane preparations and effects of altering $[K^+]_o$. Journal of Pharmacological and Toxicological Methods 2004, 50, 187-199.). Briefly, drug dilutions were prepared from 10 mM dimethyl sulfoxide stocks and the following were added to a 96-well polystyrene plate (Perkin-Elmer Optiplate): 20 µL of assay binding buffer (for total bounds), or 1 µM astemizole (for non-specific bounds), or test drug, 50 µL of [³H]dofetilide (20 nM, ~80 Ci/mmol specific activity), and 130 µL of membrane homogenate (final protein concentration of 30 µg per well). The plates were incubated at ambient temperature for 45 minutes, aspirated onto GF/B filter plates (Perkin-Elmer), and washed with 2 mL of cold wash buffer. After allowing the plates to dry, 50 µL of scintillant (Perkin-Elmer MicroScint 20) were added to each well and the radioactivity was counted in a Perkin-Elmer Topcount NXT scintillation counter. $IC_{50}$ determinations were calculated from competition curves using 6 drug concentrations, half-log apart, starting at a high concentration of 100 µM (final assay dimethyl sulfoxide concentration=1%) using a four-parameter logistic equation. $K_i$ values were derived from the calculated $IC_{50}$ values by using the Cheng and Prusoff (Cheng, Y.; Prusoff, W. H. Relationship between the inhibition constant ($K_I$) and the concentration of inhibitor which causes 50 percent inhibition ($I_{50}$) of an enzymatic reaction. Biochemical Pharmacology 1973, 22(23), 3099-3108) equation ($K_i=IC_{50}/1+[\text{ligand}]/K_d$) using $K_d$ values for [³H]dofetilide obtained from saturation assays previously described (Diaz et al., 2004).

Table 2 lists the results for representative compounds of the present invention.

TABLE 2

Selected Examples of [³H]dofetilide Binding

| Example No. | dofetilide binding, $K_i$ (µM) |
|---|---|
| 2 | >53 |
| 3 | 13 |
| 4 | 16 |
| 5 | 19 |
| 6 | >54 |
| 7 | 8.5 |

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound of formula (I):

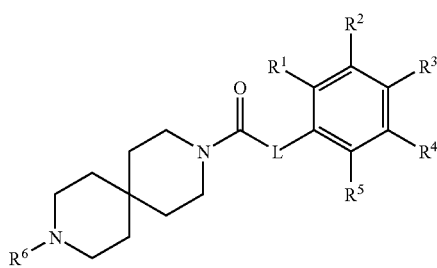

(I)

or a pharmaceutically acceptable salt thereof, wherein
L is a bond, $CH_2$, or $NR^7$;
$R^1$, $R^2$, $R^3$, $R^4$ and $R^5$ are each independently selected from hydrogen, halogen, and methoxy, wherein at least one of $R^1$, $R^2$, $R^3$, $R^4$ and $R^5$ is halogen and at least one of $R^1$, $R^2$, $R^3$, $R^4$ and $R^5$ is methoxy;
$R^6$ is hydrogen or methyl; and
$R^7$ is hydrogen or alkyl.

2. The compound according to claim 1 of formula (I), wherein $R^6$ is hydrogen.

3. The compound according to claim 1 of formula (I), wherein $R^6$ is methyl.

4. The compound according to claim 1 of formula (I), wherein L is a bond.

5. The compound according to claim 1 of formula (I), wherein L is $CH_2$.

6. The compound according to claim 1 of formula (I), wherein L is $NR^7$.

7. The compound according to claim 1 of formula (I), wherein L is a bond and $R^6$ is hydrogen.

8. The compound according to claim 1 of formula (I), wherein L is a bond and $R^6$ is methyl.

9. The compound according to claim 1 of formula (I), wherein L is a $CH_2$ and $R^6$ is methyl.

10. The compound according to claim 1 of formula (I), wherein L is $NR^7$, wherein $R^7$ is hydrogen, and $R^6$ is methyl.

11. The compound of claim 1, selected from the group consisting of:
    3-(4-fluoro-3-methoxybenzoyl)-3,9-diazaspiro[5.5]undecane;
    3-(4-fluoro-3-methoxybenzoyl)-9-methyl-3,9-diazaspiro[5.5]undecane;
    3-(3-fluoro-4-methoxybenzoyl)-9-methyl-3,9-diazaspiro[5.5]undecane;
    3-(3-chloro-4-methoxybenzoyl)-9-methyl-3,9-diazaspiro[5.5]undecane;
    3-(3,5-dichloro-4-methoxybenzoyl)-9-methyl-3,9-diazaspiro[5.5]undecane;
    3-(3-chloro-4,5-dimethoxybenzoyl)-9-methyl-3,9-diazaspiro[5.5]undecane;
    N-(3-fluoro-4-methoxyphenyl)-9-methyl-3,9-diazaspiro[5.5]undecane-3-carboxamide;
    N-(3-chloro-4-methoxyphenyl)-9-methyl-3,9-diazaspiro[5.5]undecane-3-carboxamide;
    N-(5-chloro-2,4-dimethoxyphenyl)-9-methyl-3,9-diazaspiro[5.5]undecane-3-carboxamide; and
    3-[(3-fluoro-4-methoxyphenyl)acetyl]-9-methyl-3,9-diazaspiro[5.5]undecane.

12. A pharmaceutical composition comprising a therapeutically effective amount of a compound of claim 1, or a salt thereof, in a pharmaceutically acceptable carrier.

* * * * *